Figures 1, 2:
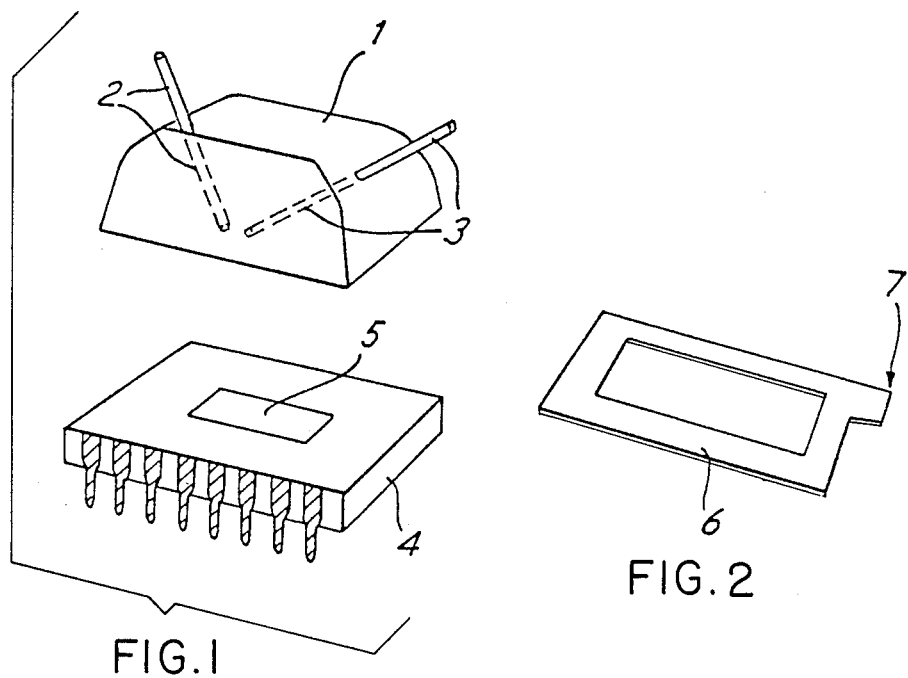

United States Patent [19]

Sibbald et al.

[11] Patent Number: 4,865,716
[45] Date of Patent: Sep. 12, 1989

[54] SENSOR ARRANGEMENTS

[75] Inventors: Alastair Sibbald, Maidenhead; Peter D. Whalley, Slough, both of England

[73] Assignee: Thorn EMI plc, London, England

[21] Appl. No.: 218,960

[22] Filed: Jul. 14, 1988

[30] Foreign Application Priority Data

Jul. 18, 1987 [GB] United Kingdom ............... 8717036

[51] Int. Cl.⁴ .......................... G01N 27/30; C09J 5/00
[52] U.S. Cl. .................................. 204/409; 156/295; 156/305; 204/416; 357/25
[58] Field of Search ............... 156/305, 295; 204/409, 204/416; 357/25

[56] References Cited

U.S. PATENT DOCUMENTS 3,767,211 10/1973 Amphlett ................................. 277/1
3,915,829 10/1975 Krebs ..................................... 204/435
4,514,263 4/1985 Janata .................................... 204/1 T
4,671,852 6/1987 Pyke ...................................... 156/652
4,764,797 8/1988 Shaw et al. ........................... 357/25

Primary Examiner—G. L. Kaplan
Attorney, Agent, or Firm—Fleit, Jacobson, Cohn, Price, Holman & Stern

[57] ABSTRACT

A sensor arrangement is described in which a semi-conductor component, such as an ion-selective field-effect transistor (ISFET) is secured to a ducting component containing ducts to carry fluid towards and away from a sensitive region of the ISFET. The two components are secured together by means of a gasket formed of porous material and apertured where adhesion of the components to one another is not required. The gasket is inserted between the components and adhesive applied to an exposed portion, such as a tab, of the gasket. The adhesive is distributed by capillary action to all parts of the gasket and secures the components together without affecting those areas of the components juxtaposed with the apertured region or regions of the gasket.

4 Claims, 1 Drawing Sheet

SENSOR ARRANGEMENTS

This invention relates to sensor arrangements and it relates more particularly to such arrangements in which there is a need to form reliable and robust, fluid-tight seals between components of compact arrangements, for example those based upon the use of ion-selective field effect transistors.

Such arrangements are well known for use in the sensing of particular constituents in samples of biological liquids and are well established for medical sampling purposes. For such purposes, it is necessary for the relevant liquid under test to be conveyed to the vicinity of a sensitized gate region of a field effect transistor (FET) and, since it would be extremely difficult to manufacture the FET integrally with a component containing ducting for the liquid under test, this invention provides for the two components, i.e. the ducting component and the semiconductor (FET) component, to be produced separately and then secured reliably together. In addition to the need for the two components to be reliably and robustly secured together, it is also vital to ensure that the jointing material does not interfere in any way with the ducting, because free flow of liquid to and from the FET sensor is essential.

According to the invention there is provided a sensor arrangement including a semiconductor component capable of responding to one or more constituents likely to be present in a fluid under test, and a ducting component formed with ducting to convey said fluid towards and away from a region of said semiconductor component that is sensitive to said one or more constituents, the ducting component being secured to the semiconductor component by means of an adhesive applied to an exposed region of a gasket pre-formed to define those areas of the two components to be secured together, the gasket being sufficiently porous in relation to the flow characteristics of the adhesive as to cause the adhesive to migrate to said areas but to no other regions between the two components.

In order that the invention may be clearly understood and readily carried into effect, one embodiment thereof will now be described, by way of example only, with reference to the accompanying drawing, of which:

FIG. 1 shows a pair of components to be secured together to form a sensor arrangement in accordance with one example of the invention, and FIG. 2 shows a porous gasket for use in securing together the two components shown in FIG. 1.

Referring now to the drawings, FIG. 1 shows the attachment of a perspex flow-cap 1, containing ducts, 2 and 3, to a 16-pin ceramic header 4 housing an ion-selective field-effect transistor (ISFET) shown schematically at 5, to form a solution-resistant join. A porous gasket 6, as shown in FIG. 2, is configured to define those areas at which the two components, i.e. the cap 1 and the header 4, are to be secured together. The gasket 6 which may be made of filter paper is then placed appropriately between the cap 1 and the header 4, and a liquid adhesive (not shown) is applied to an exposed region 7 of the porous gasket, whereby capillary action ensures a complete and uniform distribution of the adhesive throughout the porous gasket, ensuring that, after the adhesive cures, a firm bond which is free from leakage pathways is achieved between the components by virtue of the capillary nature of the application of the adhesive. The adhesive may comprise a silicone rubber diluted with xylene.

By way of example, this can be achieved using filter paper as the porous gasket and silicone rubber (e.g. Dow Corning RTV 3140) as the adhesive, appropriately diluted with xylene to provide control of viscosity.

Importantly, the adhesion between the two components is provided precisely where it is desired, and nowhere else, thus ensuring that adhesive does not foul the ducts or contaminate the sensitive surface of the FET. Moreover, the positioning of the various elements of an assembly can be controlled precisely, prior to the application of adhesive. Furthermore, the capillary action of the porous gasket ensures high integrity of the bond between the components by uniform distribution of the adhesive.

The invention is applicable to sensor arrangements requiring the joining of non-planar elements to form complex assemblies in a similar manner to that described in relation to FIGS. 1 and 2, and is also applicable to the formulation of multi-element assemblies, using one or more porous gaskets, permitting simultaneous bonding of the multiple elements, achieved through the use, for example, of an adhesive reservoir in the uppermost element and connection of the various gaskets by means of interconnecting tubes or conduits.

We claim:

1. A sensor arrangement including a semiconductor component capable of responding to one or more constituents likely to be present in a fluid under test, and a ducting component formed with ducting to convey said fluid towards and away from a region of said semiconductor component that is sensitive to said one or more constituents, the ducting component being secured to the semiconductor component by means of an adhesive applied to an exposed region of a gasket pre-formed to define those areas of the two components to be secured together, the gasket being sufficiently porous in relation to the flow characteristics of the adhesive as to cause the adhesive to migrate to said areas but to no other regions between the two components.

2. An arrangement according to Claim 1 wherein said semiconductor component comprises an ion-selective field-effect transistor.

3. An arrangement according to Claim 1 wherein said gasket is made of filter paper and the adhesive is a silicone rubber diluted with xylene.

4. An arrangement according to Claim 1 wherein the facing surfaces of said semiconductor component and said ducting component are substantially planar and said gasket is configured in two-dimensional form.

* * * * *